United States Patent [19]

Dumitrescu et al.

[11] 4,064,870

[45] Dec. 27, 1977

[54] METHOD AND DEVICE FOR EVALUATING NERVE IMPULSE PROPAGATION VELOCITY AND LATENCY OF ELECTRODERMAL REFLEXES

[75] Inventors: Ioan Florin Dumitrescu; Constantin Cojocaru; Constantin Bolintineanu, all of Bucharest, Romania

[73] Assignee: Centrul de Protectia si Igiena Muncii, Bucharest, Romania

[21] Appl. No.: 687,656

[22] Filed: May 19, 1976

[51] Int. Cl.² ............................................. A61B 5/05
[52] U.S. Cl. .................................................. 128/2 N
[58] Field of Search .................... 128/2 N, 2 R, 2.1 Z; 273/1 E; 35/22 R

[56] References Cited

U.S. PATENT DOCUMENTS

| | | | |
|---|---|---|---|
| 2,736,313 | 2/1956 | Mathison | 128/2.1 Z |
| 3,698,385 | 10/1972 | Low et al. | 128/2 N |
| 3,841,316 | 10/1974 | Meyer | 128/2.1 Z |
| 3,898,983 | 8/1975 | Elam | 128/2 N |

FOREIGN PATENT DOCUMENTS 1,466,799  4/1969  Germany .......................... 128/2 N

OTHER PUBLICATIONS

Houghton et al., "Behavior Research Methods & Instruments," vol. 5, No. 3, May 1973, pp. 273-276.

*Primary Examiner*—William E. Kamm
*Attorney, Agent, or Firm*—Karl F. Ross

[57] ABSTRACT

The method and reactometric device provide for separate or simultaneous evaluation of latency and electrodermal reflex propagation speed through postganglionic sympathetic nerve fibers. Evaluation is carried out by help of electronic interval counting devices and yields certain correlations enabling differentiation between the central and peripheral neurovegetative fatigue as well as intoxication phenomena of peripheral vegetative fibers. Evaluations are conducted through two electrodes located on the same innervation area, i.e. on the longitudinal axis of palm, the electrodes being spaced by a known distance which is considered in the evaluation of electrodermal reflex propagation. The first electrode intercepts the electrodermal reflex used in the evaluation of latency.

3 Claims, 3 Drawing Figures

METHOD AND DEVICE FOR EVALUATING NERVE IMPULSE PROPAGATION VELOCITY AND LATENCY OF ELECTRODERMAL REFLEXES

FIELD OF THE INVENTION

The invention relates to a method of and an apparatus for automatic evaluation of nerve-impulse propagation velocity through sC type vegetative nerve fibers, concurrently with the latency preceding the appearance of electrodermal reflexes for determining the neurovegetative reactivity of man under stress conditions and in intoxications with neurotrophic compounds; the method can also be applied to functional examinations in neurology.

BACKGROUND OF THE INVENTION

There are several methods which can be applied in order to test the propagation speed of nerve impulses through the motor fibers by evaluating the lag period in the appearance of motor-reaction in the successive stimulations performed at different levels on a motor-nerve tract. It is also known to evaluate the propagation velocity of nerve impulses through the sensitive nerve fibers by recording the working current induced by a single distal excitation of sensitive nerve endings, at two different levels on a peripheral nerve tract. These methods are currently applied in neurological investigations.

It is also known that electrodermal reflexes appear — with an increasing latency — in intense fatigue states under stress conditions, under diffuse hyperexcitation of nervous system as well as in nerve intoxication. The vegetative nervous fibers exhibit an increased sensitivity to the absence of oxygen and to the action of carbon dioxide and certain nerve toxins.

Evaluation of an increased latency of electrodermal reflexes in all the above-mentioned cases requires the limitation of central nervous disorders comparative to peripheral disorders. On the other hand, the decrease of nerve-impulse-propagation velocity through the peripheral vegetative fibers is an important factor in nervous disorders. The increase or decrease in nerve-impulse-propagation velocity evidences a series of pathological or physiological states. Such as hyperexcitation or fatigue, having one common characteristic, i.e. the increase in the latency of electrodermal reflexes.

SUMMARY OF THE INVENTION

Simultaneous evaluation of nerve-impulse-propagation velocity through vegetative fibers and latency of electrodermal reflexes which represent the objective of our invention avoids the above mentioned disadvantages owing to the application of a stimulus, i.e. electrical, optical or any other stimulus and provides for the recording of electrodermal reflex induced by this stimulus at two different levels; the recording is made with the use of two palm electrodes placed in a common innervation area as well as of a control (reference) electrode. This recording system permits evaluation of the lag period between stimulus application and appearance of first electrodermal reflex, i.e. the latency as well as the time required for the propagation of nerve impulse between the first and the second palm electrode; in this way the nerve-impulse-propagation velocity may be inferred because the distance between the two electrodes is known.

The device for automatic evaluation of nerve impulse propagation velocity through vegetative fibers as well as the recording of electrodermal reflex latency, according to out invention, uses a stimulus generator and two identical electrodermal reflex transducers, i.e. transducers responsive to electrical potential or resistance, with corresponding amplifiers which receive the bioelectrical signal through two palm electrodes placed at a fixed, known distance. The electrodes placed on the dorsal surface of the palm are used as reference electrodes ; the output signal of the transducers controls ,through two level comparators, a flip-flop circuit and the impulse generated by the flip-flop circuit controls the operation of an pulse generator producing impulses which are counted by help of a counter. In this manner, as the duration of impulse is known and the signal/pause ratio is equal to unity, the propagation velocity of nerve impulse may be obtained by dividing the distance between the electrodes by twice the product of impulse number and duration. For the evaluation of electrodermal reflex latency, the device possess a second flip-flop circuit controlled by the signal of stimulus generator and at return by the electrodermal reflex captured by the nearest transducer. The impulse generated by this flip-flop circuit controls the operation of a pulse generator producing impulses which are counted by a counter, in such a way that if the duration of an impulse is known and the ratio signal/pause is equal to unity, the latent period is equal twice the product of impulse number and duration.

SPECIFIC DESCRIPTION

The method of neurovegetative reactivity testing according to the invention is based, as mentioned above, on the simultaneous extrapolation of the latency in the appearance of electrodermal reflexes and propagation velocity of nerve impulse in the peripheral vegetative fibers.

The latency, i.e. period preceding the appearance of electrodermal reflexes is the time period between generation of a stimulus (optical, acustical, etc.) and appearance of electrodermal reflex generated by this stimulus and intercepted at a certain recording level. This latency depends on the functional status of the control nerve centers identified — through the electrodermal activating center — with the reticular ascendant activating system possessing different cortical areas as well as a bulbar inhibitory area.

Latency may also be defined as the sum of all central synaptic lag periods and axon transmissions.

Nerve impulse propagation velocity through vegetative fibers does not require a definition, the concept being clear from the terms used.

It is especially important to know the value of these two parameters as they may be used in the calculation of a series of intermediary periods of electrodermal reflex latency which permit the analysis of neurovegetative reactivity of the subject under investigation.

The evaluation method of both the above mentioned parameters results from their definition. In this way, the latency is evaluated by the time interval ranging between $t_o$ FIG. 2, i.e. stimulus generation and $t_1$, i.e. appearance of electrodermal reflex. Nerve-impulse-propagation velocity is evaluated by successive recordings of the electrodermal reflex, corresponding to a single stimulus, i.e. sensitive or sensory, at two different levels. If the distance between the two transducers is known, the propagation velocity may be evaluated by simple division.

Figure 1:
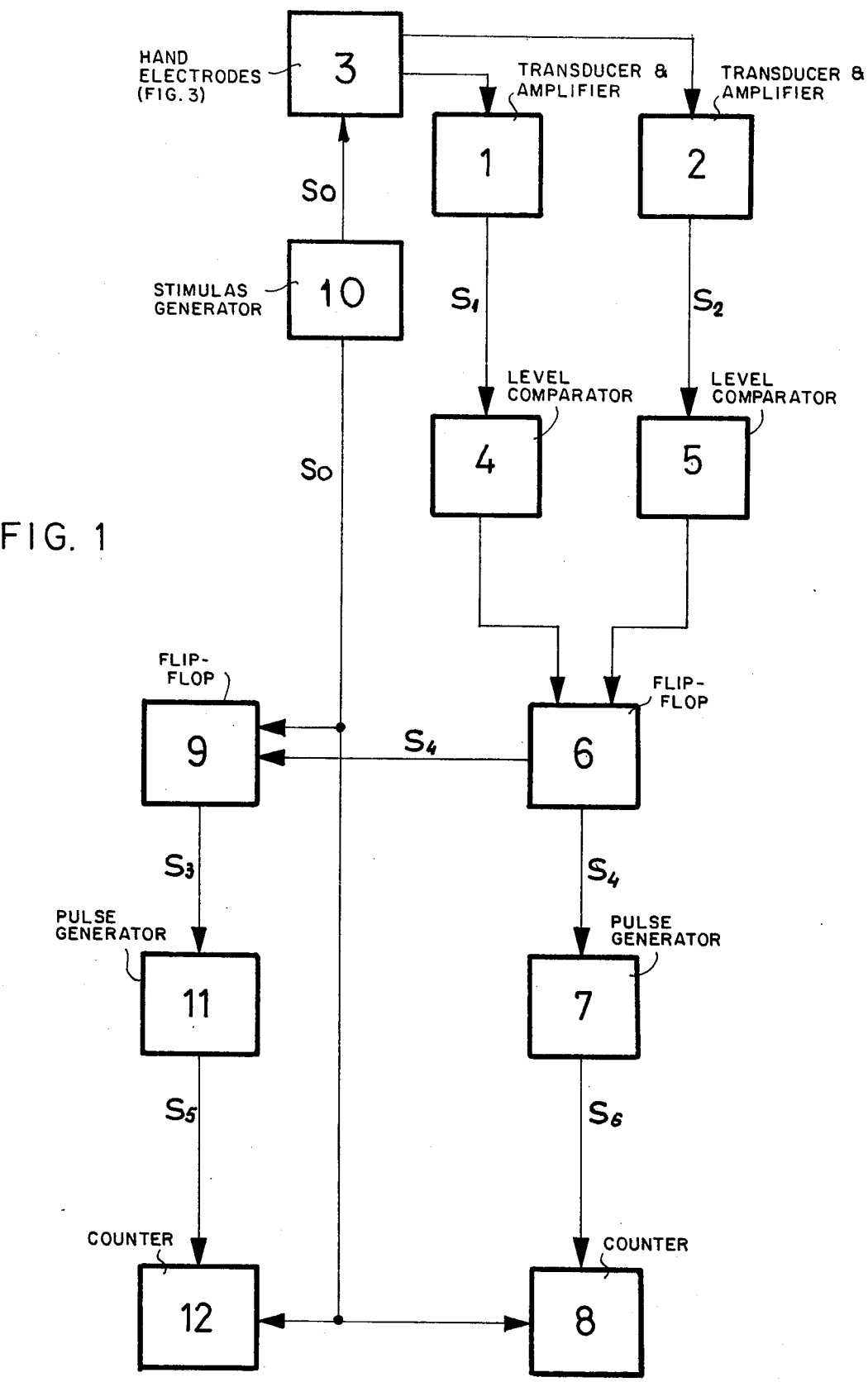
FIG. 1 is a block diagram in the drawings of the device.

According to the invention the device is provided with two identical transducers, i.e. potential or resistance corresponding to the electrodermal reflexes 1 and 2 and possessing two amplifiers. The transducers intercept the bioelectric signal through two palm electrodes A and respectively B, located at a fixed, known distance and through one reference electrode C, located on the hand dorsal surface of the subject under investigation, noted as 3 in FIG. 1 (see FIG. 3). Electrical output signal of transducers 1 and 2 is applied to two identical level comparators, 4 and 5, which control both setting and resetting of the flip-flop circuit 6. The flip-flop circuit controls an a pulse generator, 7, producing impulses which are counted by the counter 8. The setting of a second flip-flop circuit 9 is triggered by the instantaneous impulse generated by the stimulus generator 10, while the return is controlled by the first electrodermal reflex (intercepted by transducer 1 at $t_1$ through the flip-flop circuit 6. The flip-flop circuit 9 controls through its two states the on and off operation of a second pulse generator 11 producing pulses which are counted by the counter 12.

Operation of the device according to the invention is described below.

The waveforms of the electric signal in different points, on the scheme, noted as $S_o$ . . . $S_6$ and possessing a significance which will be mentioned in the following lines, are presented in the FIG. 2.

Figure 2:
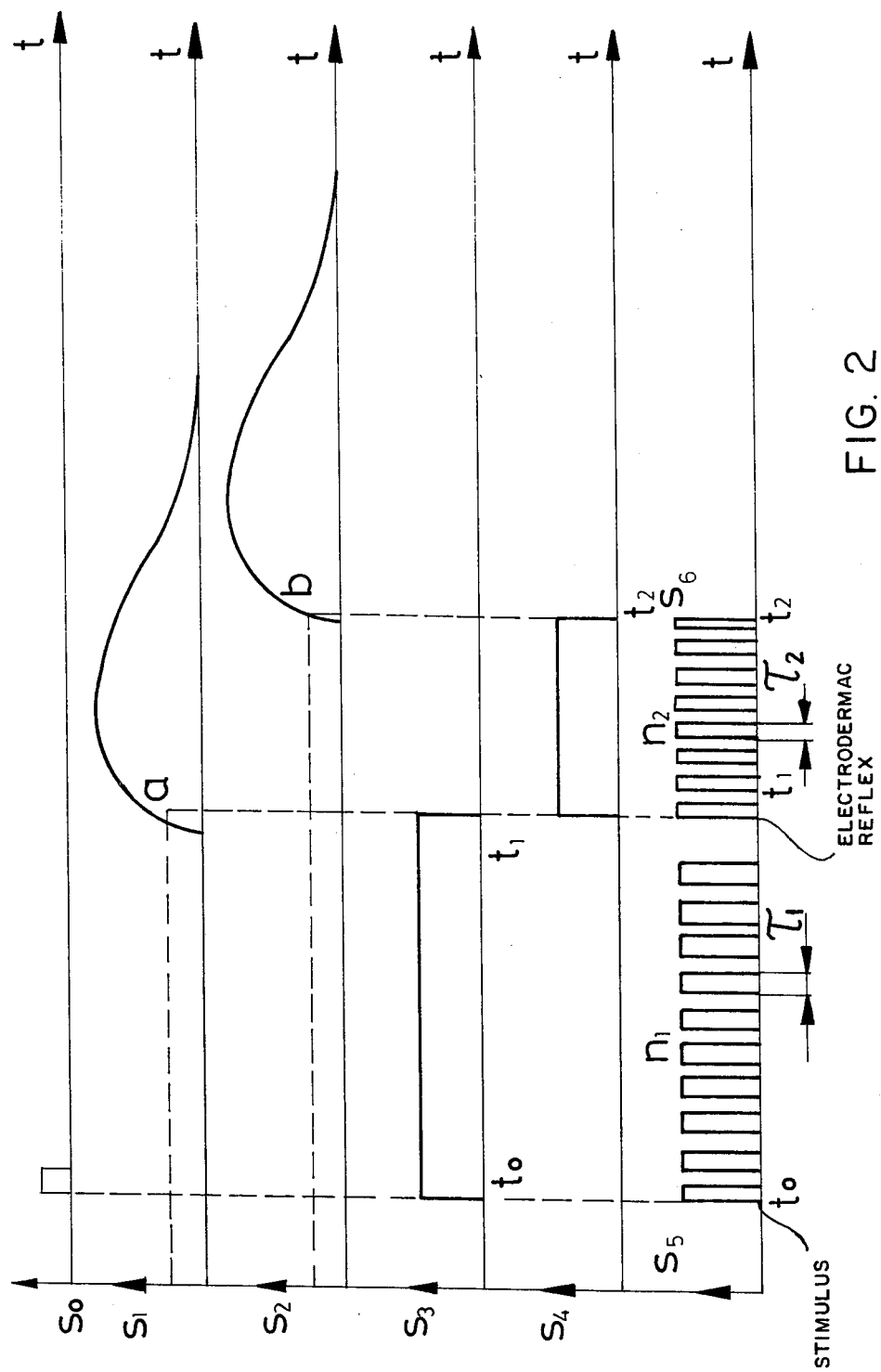
FIG. 2 is a diagram of the signal at certain points of the device.

As is apparent from FIG. 2, at the initial moment to an acoustic, optical or another kind of signal generated by the pulse generator 10 and noted as $S_o$ is applied through $t_o$ to the subject 3. The electric signal which releases stimulus generation is applied simultaneously to the flip-flop circuit resulting in its conversion from the output zero signal to the output $S_3$ signal. The $S_3$ signal induces the release of pulse generator 11, generating impulses noted as $S_5$ in FIG. 2. with a space factor equal to unity and duration $\tau_1$. These impulses are counted by the counter 12. The counting ceases when the pulse-generator 11 stops, i.e. at the appearance at the moment $t_1$, of the first electrodermal reflex beyond a given level noted as $S_1$ and intercepted by the electrode of the transducer 1. This electrodermal reflex controls through the level comparator 4 the setting of the flip-flop circuit 6 from the output zero signal state to the output signal 4 state, and the return of flip-flop circuit 9 to the output zero signal state (the return to zero of the flip-flop circuit 9 output signal, results in the stopping of the impulse generator 11). The number of impulses generated by the impulse generator 11 in the time interval $t_o - t_1$, is noted as n 1 in FIG. 2. This time interval represents the time (interval) of latency in the appearance of electrodermal reflex and it may be obtained — as it may be noted — by evaluating the product $2(n \, 1 \times \tau_1)$.

The setting of flip-flop circuit 6 in the state of output signal $S_4$ induced by the $S_1$ signal according to the first electrodermal reflex, results in the release of pulse-generator 7, generating impulses noted as $S_6$ in FIG. 2, with a ratio signal/pause equal to unity and a duration of $\tau_2$; these impulses are counted by the counter 8. The counting ceases when the impulse generator 7 stops, i.e. at the appearance, in the moment, of the electrodermal reflex intercepted by the transducer 2, with the B electrode. The electrodermal reflex noted as $S_2$ controls, through the level comparator 5 (when exceeding a certain b level), the return of the flip-flop circuit 6 by output zero signal state, i.e. the stopping of impulse generator 7. The number of pulses generated by the impulse generator 7 in the time period $t_1 \ldots t_2$ is noted as $n_2$ in FIG. 2. This interval represents the time necessary to the nerve impulse to propagate between the electrodes A and B and it may be evaluated by the the product $2n_2$. Dividing the distance between the electrodes A and B (in meters) by the time interval $2n_2\tau_2$ (in seconds) the nerve impulse propagation velocity (m/sec) may be obtained.

It may be noted that both latency of electrodermal reflex and propagation velocity of nerve impulse are proportional to the numbers $n_1$ and $1/n_2$ ( $\tau_1 \tau_2$, and the distance between the electrodes are constant). In this way the setting-up device of these numbers may be standardized to indicate directly the latency of electrodermal reflex and propagation velocity of nerve impulse. Upon the triggering of a new stimulus ; the above mentioned cycle is repeated.

Figure 3:
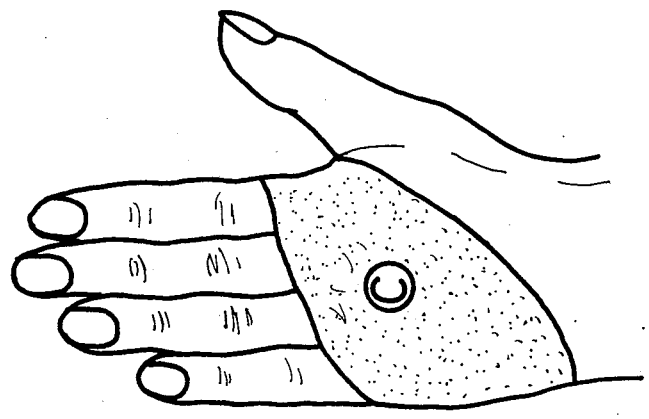
FIG. 3 shows the application of the electrodes.
Figure 3:
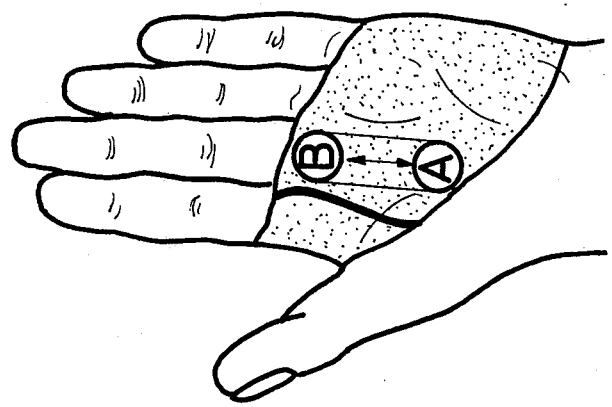

The electrodes of the device, are disposed in the pattern, shown in FIG. 3. Both passive electrodes are made either of lead plates in case of intercepting electrodermal reflex of potential and of silver plates in case of electrodermal reflex of potential. The A and B electrodes are fixed on a palm rubber sleeve at a fixed and known distance. The reference electrode C which is used as a control for the discharge electrodes A and B, is fixed by the same sleeve on the dorsal surface of the hand.

Operation of the device is conducted when the subject at rest, sitting. Two values may be obtained in the above mentioned way, one value representing the latency of electrodermal reflex and the other the propagation velocity of nerve impulse inducing the reflex through the vegetative fibers. The two values, compared to the normal values obtained in case of subjects in a certain activity conditions conduct to important conclusions in the diagnosis of neuropsyhical disorders.

Particularly, if an extension of latency is noted it may be checked if this is accompanied or not, by a modification in propagation velocity of the nerve impulse.

The method and device have the following advantages: they ensure simplicity of operation without nuisance for the subject under investigation;

The device can be transistorized and autonomous 3 and the system ensures a high precision in evaluation of neurovegetative reactivity disorders.

We claim:

1. A method of evaluating nerve-impulse-propagation velocity through vegetative fibers of a human subject and the latency of electrodermal reflexes, comprising the steps of:
    disposing two electrodes with a predetermined spacing on the palm of the hand of a subject in a common innervation area;
    generating a stimulus to trigger a nerve response in said subject;
    initiating the product of a train of first pulses simultaneously with the generation of said stimulus;
    counting said first pulses;
    terminating the counting of said first pulses upon detection of an electrodermal reflex at one of said electrodes, the resulting count of the first pulse representing the period of latency of electrodermal reflexes;

initiating a train of second pulses upon the detection of the electrodermal reflex at said one of said electrodes;

counting said second pulses;

terminating the counting of said second pulses upon the detection of a corresponding electrodermal reflex at the other of said electrodes; and establishing the nerve-impulse progagation velocity of the subject by dividing the distance between said electrodes by the sum of the pulse durations and pulse intervals of the counted second pulses.

2. A device for the evaluation of nerve-impulse-propagation velocity through vegetative fiber of a human subject and the latency of electrodermal reflexes thereof, said device comprising:

a pair of palm electrodes and means for holding said palm electrodes with a predetermined spacing against a common innervation area of the palm of said subject;

a stimulus generator for exciting in said subject a nerve response;

respective transducers connected to said electrodes for producing output signals representing electrodermal responses at each of said electrodes;

respective level comparators connected to said transducers for producing respective outputs upon the output signals of the respective transducers exceeding predetermined levels;

a first flip-flop circuit triggerable into one state by the outputs of one of said level comparators and into an opposite state by the output of the other of said level comparators;

a first pulse generator connected to said first flip-flop and triggerable thereby in said one state of said flip-flop to produce a train of first pulses during the interval between said states of said first flip-flop; and a first counter connected to said first pulse generator for counting said first pulses during said interval, the nerve-impulse-propagation velocity being determined by dividing the distance between said electrodes by said interval as determined by the count of said first counter.

3. The device defined in claim 2, further comprising:

a second flip-flop triggered by said stimulus generator into one state and by said first flip-flop into another state;

a second pulse generator connected to said second flip-flop for generating a train of second pulses upon triggering of said second flip-flop into its said one state; and a second counter connected to said second pulse generator for counting the second pulses generated thereby during the interval between said one and said other states of said second flip-flop, the count of said second pulses representing the latency of electrodermal reflexes of said subject.

* * * * *